United States Patent [19]

Doyle et al.

[11] Patent Number: 4,508,694

[45] Date of Patent: Apr. 2, 1985

[54] SEPARATION AND RECOVERY OF CARBON MONOXIDE BY COPPER (I) COMPLEXES

[75] Inventors: Gerald Doyle, Whitehouse Station; Roy L. Pruett, New Providence; David W. Savage, Lebanon, all of N.J.

[73] Assignee: Exxon Research & Engineering Co., Florham Park, N.J.

[21] Appl. No.: 492,173

[22] Filed: May 6, 1983

[51] Int. Cl.³ .............................................. B01D 53/34
[52] U.S. Cl. .............................. 423/246; 423/415 A; 55/68
[58] Field of Search ................ 55/56, 68; 423/415 A, 423/246

[56] References Cited

U.S. PATENT DOCUMENTS

| 2,930,672 | 3/1960 | Morris | 423/246 |
| 3,337,291 | 8/1967 | Clay | 423/246 |
| 3,630,676 | 12/1971 | Davis et al. | 423/415 A |
| 3,658,463 | 4/1972 | Billings | 423/246 |
| 4,048,292 | 9/1977 | Green | 423/415 A |
| 4,102,802 | 7/1978 | Johnson et al. | 423/246 |
| 4,279,874 | 7/1981 | Doyle | 423/246 |
| 4,347,066 | 8/1982 | Doyle | 423/415 A |
| 4,387,055 | 6/1983 | Doyle | 423/246 |

*Primary Examiner*—Howard S. Williams
*Assistant Examiner*—Terryence Chapman
*Attorney, Agent, or Firm*—James H. Takemoto; Edward H. Mazer

[57] ABSTRACT

Carbon monoxide is removed from feedstreams by a process which comprises contacting the feedstream with a solution of a cuprous fluorinated acetylacetonate in an organic solvent containing a stabilizing agent to remove CO by forming a first cuprous complex, decomposing the first cuprous complex whereby the stabilizing agent which replaces CO in the first cuprous complex to form a second cuprous complex, and separating the displaced CO. The formation of the second cuprous complex avoids any deposition of copper metal upon heating.

14 Claims, No Drawings

SEPARATION AND RECOVERY OF CARBON MONOXIDE BY COPPER (I) COMPLEXES

BACKGROUND OF THE INVENTION

This invention relates to the removal and recovery of carbon monoxide from feedstreams. More particularly, carbon monoxide is removed from feedstreams by formation of a complex with Cu(I)-fluorinated acetylacetonate in the presence of a stabilizing agent which prevents disproportionation of the complex to copper metal during recovery of carbon monoxide.

It is well-known that cuprous salt solutions will absorb carbon monoxide (CO). A review of the early literature relating to this topic may be found in J. Appl. Chem. (London), 15, 17–28(1965). It is also known that certain silver(I) and copper(I) salts form complexes with olefins and acetylenes. For example, cuprous chloride is known to form complexes with both ethylene and acetylene. U.S. Pat. No. 3,401,112 teaches a method of separating a mixture of hydrocarbons having differing degrees of unsaturation using a copper(I) salt of the formula CuXA where XA is an anion, X is oxygen or fluorine and A is the remainder of the anion. Examples of fluorinated anions include fluoro substituted carboxylates, fluorosulphonate, perfluoroborate, hexafluorophosphate and hexafluoroantiomonate. CuXA forms a cuprous complex with said unsaturated hydrocarbon. Similarly, U.S. Pat. No. 3,517,079 describes a process for separating vinyl aromatic hydrocarbons from alkyl aromatic hydrocarbons using a cuprous fluoroborate or cuprous fluorophosphate salt wherein a complex is formed. U.S. Pat. Nos. 3,754,047 and 3,755,487 relate to a process for separating complexible ligands such as olefins, acetylenes, aromatics and CO from a feedstream using cuprous salts such as $CuAlCl_4$, $CuBF_4$, $CuOOCCF_3$, $CuPF_6$ and the like. A process for separating CO from gas mixtures using copper(I) salts of sulfonic acids or dialkyl phosphates is disclosed in U.S. Pat. No. 4,042,669. U.S. Pat. No. 4,048,292 teaches a method for preparing high purity CO from $CO_2$-free gas streams using a copper ammonium $C_1$–$C_2$ acetate as the absorbent medium. Finally, U.S. Pat. No. 4,279,874 describes a process for removing CO from a gas stream wherein the gas stream is contacted with an absorbent solution containing a Cu(I) complex with halogenated beta-diketonate as ligand thereby removing CO as a carbonyl-Cu(I)-halogenated beta-diketonate complex.

The known processes for removing CO by Cu(I) complex formation suffer from one or more disadvantages such as high corrosivity, low reactivity to CO, high energy cost to regenerate CO, low selectivity to CO, instability of the absorbent system and formation of Cu metal during regeneration of absorbent solution. It would be highly desirable to have a method for selectively and efficiently removing CO and unsaturated hydrocarbon from a feedstream while at the same time being able to regenerate the absorbent system under mild conditions without formation of copper metal.

SUMMARY OF THE INVENTION

It has been discovered that CO can be selectively absorbed from feedstreams using Cu(I) salts and the Cu(I)-containing absorbent regenerated without depositing metal from solution. Accordingly, there is provided a process for separating carbon monoxide from a feedstream without copper metal formation which comprises the steps of:

(a) contacting the feedstream with a solution of a cuprous fluorinated acetylacetonate of the formula

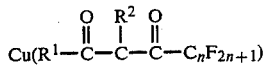

where $R^1$ is $C_1$–$C_6$ fluoroalkyl, $C_1$–$C_8$ alkyl, $C_4$–$C_6$ heterocycle containing O, S or N or $C_6$–$C_{10}$ aryl, $R^2$ is H or $C_1$–$C_6$ alkyl with the proviso that $R^1$ and $R^2$ together with the carbons to which they are attached may be joined together to form a $C_6$ ring, and n is an integer from 1 to 8, in an organic solvent containing a stabilizing agent at a temperature sufficient to remove carbon monoxide by forming a first Cu(I) complex of the formula

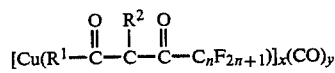

where $R^1$, $R^2$ and n are defined above, and x and y are 1 or 2, said stabilizing agent being characterized by replacing CO in the first Cu(I) complex thereby forming a second Cu(I) complex which is stable at temperatures wherein the first Cu(I) complex decomposes through loss of CO, (b) heating to a temperature sufficient to decompose the first Cu(I) complex through loss of CO whereby the stabilizing agent replaces CO in the first Cu(I) complex and copper metal formation is prevented by formation of the second Cu(I) complex, and (c) separating the carbon monoxide.

Another embodiment of the process for separating CO from feedstreams without copper metal formation comprises the steps of:

(a) contacting the feedstream with a solution of a cuprous fluorinated acetylacetonate of the formula

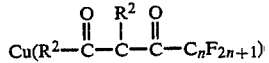

where $R^1$ is $C_1$–$C_6$ fluoroalkyl, $C_1$–$C_8$ alkyl, $C_4$–$C_6$ heterocycle containing O, S or N or $C_6$–$C_{10}$ aryl, $R^2$ is H or $C_1$–$C_6$ alkyl with the proviso that $R^1$ and $R^2$ together with the carbons to which they are attached may be joined together to form a $C_6$ ring, and n is an integer from 1 to 8, in an organic solvent containing a stabilizing agent at a temperature sufficient to remove CO by forming a first Cu(I) complex of the formula

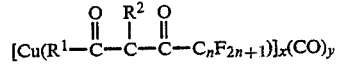

where $R^1$, $R^2$ and n are defined above, and x and y are 1 or 2, said stabilizing agent being characterized by replacing CO in the first Cu(I) complex thereby forming a second Cu(I) complex which is stable at pressures wherein the first Cu(I) complex decomposes through loss of CO, (b) reducing pressure by an amount sufficient to decompose the first Cu(I) complex through loss of CO whereby the stabilizing agent replaces CO in the first Cu(I) complex and copper metal formation is prevented by formation of the second Cu(I) complex, and (c) separating the CO.

A further embodiment of the process for separating CO from feedstreams without copper metal formation comprises the steps of:

(a) contacting the feedstream with a solution of a cuprous fluorinated acetylacetonate of the formula $$Cu(R^1-\underset{\underset{O}{\|}}{C}-\underset{\underset{R^2}{|}}{C}-\underset{\underset{O}{\|}}{C}-C_nF_{2n+1})$$

where $R^1$ is $C_1$–$C_6$ fluoroalkyl, $C_1$–$C_8$ alkyl, $C_4$–$C_6$ heterocycle containing O, S or N or $C_6$–$C_{10}$ aryl, $R^2$ is H or $C_1$–$C_6$ alkyl with the proviso that $R^1$ and $R^2$ together with the carbons to which they are attached may be joined together to form a $C_6$ ring, and n is an integer from 1 to 8, in an organic solvent containing a stabilizing agent at a temperature sufficient to remove CO by forming a first Cu(I) complex of the formula $$[Cu(R^1-\underset{\underset{O}{\|}}{C}-\underset{\underset{R^2}{|}}{C}-\underset{\underset{O}{\|}}{C}-C_nF_{2n+1})]_x(CO)_y$$

where $R^1$, $R^2$ and n are defined above, and x and y are 1 or 2, said stabilizing agent being characterized by replacing CO in the first Cu(I) complex thereby forming a second Cu(I) complex which is stable at pressures wherein the first Cu(I) complex decomposes through loss of CO, (b) reducing CO partial pressure by adding an inert gas stripping agent in an amount sufficient to strip CO from the first Cu(I) complex whereby the stabilizing agent replaces CO in the first Cu(I) complex and copper metal formation is prevented by formation of the second Cu(I) complex, (c) separating the CO.

When Cu(I) beta-diketonate complexes containing CO are decomposed to remove CO without the presence of stabilizing agent, a disproportionation reaction occurs producing copper metal and a Cu(II) salt. Processing these mixtures involves the handling of slurries containing copper metal which is disadvantageous due to difficulties presented by such slurries. The present invention avoids this problem during heating by maintaining the Cu(I) in solution as a stabilized complex.

DETAILED DESCRIPTION OF THE INVENTION

When a feedstream containing CO is contacted with cuprous fluorinated acetylacetonate solution in an organic solvent, a first cuprous complex is formed as illustrated by the following reaction:

$$xCu(R^1-\underset{\underset{O}{\|}}{C}-\underset{\underset{R^2}{|}}{C}-\underset{\underset{O}{\|}}{C}-C_nF_{2n+1}) + yCO \longrightarrow \qquad (I)$$

-continued
$$[Cu(R^1-\underset{\underset{O}{\|}}{C}-\underset{\underset{R^2}{|}}{C}-\underset{\underset{O}{\|}}{C}-C_nF_{2n+1})]_x(CO)_y$$

where $R^1$, $R^2$ and n are defined as above, and x and y are 1 or 2, preferably 1.

In order to recover CO, the cuprous complex product of reaction (I) is heated and an equilibrium is established, i.e., $$[Cu(R^1-\underset{\underset{O}{\|}}{C}-\underset{\underset{R^2}{|}}{C}-\underset{\underset{O}{\|}}{C}-C_nF_{2n+1})]_x(CO)_y \overset{\Delta}{\rightleftharpoons} \frac{x}{2}Cu + \qquad (II)$$

$$\frac{x}{2}Cu(R^1-\underset{\underset{O}{\|}}{C}-\underset{\underset{R^2}{|}}{C}-\underset{\underset{O}{\|}}{C}-C_nF_{2n+1})_2 + yCO$$

The present invention is directed to avoiding reaction (II) and this is accomplished by adding a stabilizing agent thus maintaining the cuprous complex in solution as a second cuprous complex as shown below:

$$[Cu(R^1-\underset{\underset{O}{\|}}{C}-\underset{\underset{R^2}{|}}{C}-\underset{\underset{O}{\|}}{C}-C_nF_{2n+1})]_x(CO)_y + yL^1 \rightleftharpoons [Cu(R^1-\underset{\underset{O}{\|}}{C}-\underset{\underset{R^2}{|}}{C}-\underset{\underset{O}{\|}}{C}-C_nF_{2n+1})]_x(L^1)_y + yCO \qquad (III)$$

During heating, pressure reduction or inert gas stripping, the more volatile ligand CO is driven off and separated while the stabilizing agent $L^1$ replaces CO in the first cuprous complex thus forcing the equilibrium in favor of a second cuprous complex containing $L^1$ which is more stable at higher temperatures or reduced CO partial pressures. The equilibrium of reaction (III) can be shifted in the reverse direction by lowering the temperature and contacting with CO-containing feedstream or by restoring CO pressure by contacting with CO-containing feedstream which results in reformation of $$[Cu(R^1-\underset{\underset{O}{\|}}{C}-\underset{\underset{R^2}{|}}{C}-\underset{\underset{O}{\|}}{C}-C_nF_{2n+1})]_x(CO)_y$$

which is thermodynamically more stable at lower temperatures or greater CO partial pressure and $L^1$ is displaced. This heating-cooling or CO pressure differential reaction cycle can be repeated without any noticeable formation of solids, particularly Cu metal.

The stabilizing agents $L^1$ are alkenes, alkynes, isonitriles, nitriles or sulfides, preferably alkenes, alkynes or isonitriles. Preferred alkenes, alkynes and isonitriles are (a) alkenes of the formula $$\underset{R^4}{\overset{R^3}{\diagdown}}C=C\underset{R^6}{\overset{R^5}{\diagup}}$$

where each $R^3$–$R^6$ is independently H provided that at least one of $R^3$–$R^6$ is not H; $C_1$–$C_{30}$, more preferably $C_1$–$C_{15}$ and especially $C_1$–$C_8$ aliphatic with the proviso that any combination of $R^3$, $R^4$, $R^5$ and $R^6$ may be joined together to form at least one $C_4$–$C_{14}$, more preferably $C_5$–$C_{12}$, most preferably $C_6$–$C_8$ cycloaliphatic ring; —C≡N; $C_6$–$C_{10}$ aryl; $C_7$–$C_{14}$ aralphatic;

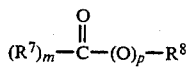

where m and p are 0 or 1, $R^7$ is $C_1$–$C_{20}$, preferably $C_1$–$C_{10}$ aliphatic, and $R^8$ is H, $C_1$–$C_{10}$ aliphatic or $C_6$–$C_{10}$ aryl with the proviso that adjacent

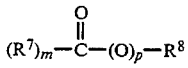

may be joined together to form a $C_4$–$C_{16}$ anhydride; (b) alkynes of the formula $R^9$—C≡C—$R^{10}$ where $R^9$ and $R^{10}$ are independently H; $C_1$–$C_{30}$, more preferably $C_1$–$C_{15}$ and especially $C_1$–$C_8$ aliphatic; $C_6$–$C_{10}$ aryl or $C_7$–$C_{14}$ araliphatic; and (c) isonitriles of the formula $R^{11}$—N≡C where $R^{11}$ is $C_1$–$C_{20}$, preferably $C_1$–$C_{10}$ aliphatic; $C_3$–$C_{10}$, preferably $C_5$–$C_7$ cycloaliphatic; $C_7$–$C_{20}$, preferably $C_7$–$C_{14}$ araliphatic or $C_6$–$C_{10}$ aryl. More preferred are $C_4$–$C_{30}$, alkenes, alkynes and isonitriles, and $C_5$–$C_{20}$ alkenes are especially preferred. The aliphatic, cycloaliphatic, araliphatic and aryl hydrocarbyl radicals may be substituted with unreactive substituents such as halogen, alkoxy, nitro and the like, and the aliphatic, cycloaliphatic or araliphatic hydrocarbyl radicals may be saturated or unsaturated.

Examples of suitable alkenes and alkynes include: 1-octene, 1,5-cyclooctadiene, stilbene, diphenylacetylene, 1-dodecene, styrene, cyclooctene, 1,5,9-cyclododecatriene, 1,3-hexadiene, isopropylacetylene, 1-decene, 1-tetradecene, 1,5-bicycloheptadiene, 1-octadecene, cyclopentene, octalin, methylene cyclohexane, diphenyl fulvene, 1-octadecyne, benzyl cinnamate, benzal acetophenone, acrylonitrile, maleic anhydride, oleic acid, linolenic acid, acrylic acid, methyl methacrylate and diethyl maleate. Suitable isontriles are, e.g., methyl isocyanide, butyl isocyanide, cyclohexyl isocyanide, phenylethyl isocyanide and phenyl isocyanide.

Nitriles and sulfides are of the formula

where $R^{12}$, $R^{13}$ and $R^{14}$ are independently $C_1$–$C_{20}$, preferably $C_1$–$C_{10}$ aliphatic; $C_3$–$C_{10}$, preferably $C_5$–$C_7$ cycloaliphatic; $C_7$–$C_{20}$, preferably $C_7$–$C_{14}$ araliphatic or $C_6$–$C_{10}$ aryl. Suitable examples include acetonitrile, propionitrile, benzonitrile, cyclohexylnitrile, benzylnitrile, dimethyl sulfide, di-n-butyl sulfide, diphenyl sulfide, dibenzyl sulfide, methyl butyl sulfide and the like.

Cuprous complexes containing $L^1$ are exemplified by:
Cu(1,5-cyclooctadiene)(hfacac), (hfacac=1,1,1,5,5,5-hexafluoroacetylacetonate),
Cu(ethylene)(hfacac),
$Cu_2$(bicyclo[2.2.1]hepta-2,5-diene)(hfacac)$_2$,
Cu(isoprene)(hfacac),
Cu(1-decene)(hfacac),
Cu(diethylmaleate)(hfacac),
Cu(styrene)(hfacac),
Cu(1,3-butadiene)(hfacac),
Cu(diphenylacetylene)$_2$(hfacac),
$Cu_2$(2,8-decadiyne)(hfacac)$_2$,
Cu(2-hexyne)(hfacac),
$Cu_2$(1,3,5,7-cyclooctatetraene)(trifluoroacetylacetonate)$_2$ and Cu(1,5-cyclooctadiene)(thenoyltrifluoroacetylacetonate)

Cuprous fluorinated acetylacetonate solutions are preferably prepared by reacting $Cu_2O$ and fluorinated acetylacetone in an organic solvent. Such solutions may be prepared, however, by other methods such as the reaction of a Cu(I) salt with a thallium fluorinated acetylacetonate salt in an organic solvent. If stabilizing agent $L^1$ is used as the organic solvent, a secondary reaction will occur in which the second cuprous complex containing $L^1$ will be formed. This has no effect on removing CO from feedstream since CO will displace $L^1$ due to thermodynamic considerations.

Preferred fluorinated acetylacetone ligands which are reacted to form cuprous fluorinated acetylacetonates have the formula

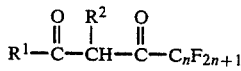

where $R^1$ is $C_1$–$C_3$ fluoroalkyl, especially $CF_3$, $C_1$–$C_8$ alkyl which may be substituted by phenyl, $C_6$–$C_{10}$ aryl or $C_4$–$C_5$ heterocycle containing O, S or N, especially S, $R^2$ is H with the proviso that $R^1$ and $R^2$ may join together to form a $C_6$ ring and n is 1 to 4, especially 1. Examples of preferred embodiments of fluorinated acetylacetones include

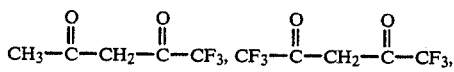

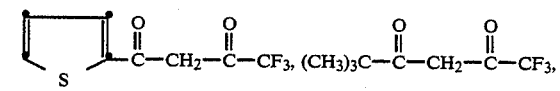

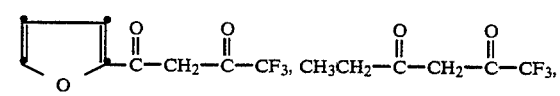

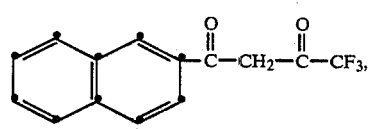

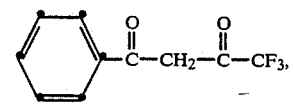

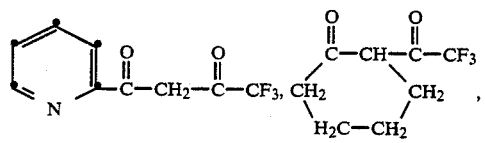

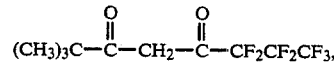

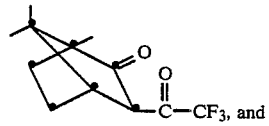

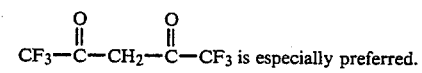

is especially preferred.

The process of the invention takes place in an organic solvent. Said solvents may be inert solvents such as ethers, ketones, esters, alcohols, saturated aliphatic hydrocarbons, aromatic hydrocarbons and the like, or they may be the stabilizing agents used as $L^1$ in reaction (III) above. It is preferred to use the stabilizing agent $L^1$ as the organic solvent because this minimizes separations problems. It is also desirable to carry out the process in an inert atmosphere since substantial amounts of oxidizing gases such as oxygen may result in the undesirable conversion of Cu(I) to Cu(II). If an inert organic solvent is employed, stabilizing agent may be present during the preparation of cuprous fluorinated acetylacetonate solution, or stabilizing agent may be added after formation of first cuprous complex pursuant to reaction (I) above. Stabilizing agent must, however, be present before decomposition of said first cuprous complex.

Reaction times are not critical, and the feed-stream is contacted with cuprous fluorinated acetylacetonate solution for a sufficient time to remove CO. Feedstreams may be easily monitored using gas or liquid chromatography for detecting removal of desired components.

For reaction (I) above, wherein the CO is being removed from feedstream by reaction with cuprous fluorinated acetylacetonate solution to form a first cuprous complex, the operating temperature for any given cuprous complex is a function of the stability of that particular cuprous complex. The decomposition temperature for any particular cuprous complex may be determined by measuring CO partial pressure as a function of temperature. Decomposition temperatures are characterized by a rapid increase in CO partial pressure as the temperature is raised. Reaction (I) may be conducted in tempratures from about $-100°$ C. to about $5°$ C. below the decomposition temperature, preferably from about $0°$ C. to about $10°$ C. below the decomposition temperature.

Substitution of $L^1$ in the first cuprous complex is exemplified by reaction (III) above and this reaction utilizes temperature, pressure differential or combination thereof to force the equilibrium of reaction (III) in favor of the second Cu(I) complex of the formula

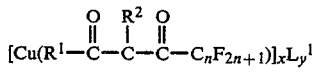

In the case of temperature, the first Cu(I) complex formed according to reaction (I) above is heated to its decomposition temperature in the presence of stabilizing agent $L^1$. Decomposition occurs pursuant to reaction (III) and $L^1$ replaced CO in said first Cu(I) complex to form a second Cu(I) complex which is stable at the abovementioned decomposition temperature. Upon separating CO and lowering the temperature below the decomposition temperature, fresh CO-containing feedstream is added thereby reversing the equilibrium of reaction (III) by forming the first Cu(I) complex, which is thermodynamically more stable at temperatures below the decomposition temperature.

Pressure differentials may be employed to decompose the first Cu(I) complex through loss of CO. In one embodiment, the pressure of the reaction system is reduced by an amount sufficient to cause decomposition and loss of CO whereby $L^1$ replaces CO in the first Cu(I) complex to form the second Cu(I) complex which has a substantially lower vapor pressure at any given temperature. Alternatively, an inert gas stripping agent such as $N_2$, noble gas, $CH_4$ and the like is used to flush the first Cu(I) complex-containing solution thereby causing the first Cu(I) complex to lose CO by reducing the overall CO partial pressure of the system. As above, $L^1$ replaces CO and the resulting second Cu(I) complex has a substantially lower vapor pressure. In either case, adding fresh feedstream containing CO reverses reaction (III) by reforming the first Cu(I) complex which is more stable in the presence of excess CO.

A combination of temperature and pressure differential may also be used to decompose the first Cu(I) complex. For example, solution containing Cu(I) complex is heated to decomposition temperatures under reduced pressure. Alternatively, heating may be done while adding an inert gas stripping agent. Such combinations will result in an enhanced rate of decomposition of the first Cu(I) complex.

Wide variations in concentration of cuprous fluorinated acetylacetonate in the reaction mixture are possible depending on the concentration of CO in the feedstream. It is preferred to maintain cuprous fluorinated acetylacetonate in an amount equal to or less than the stoichiometric amount required by the concentration of CO in the feedstream, and a slight deficiency, i.e., 0.1 to 10% is especially preferred. The concentration of $L^1$ used is not critical and may range from an amount equivalent to the concentration of Cu(fluorinated acetylacetonate)CO complex in solution in the reaction mixture to a very large excess. $L^1$ preferably serves as the organic solvent.

While the process of the invention may be carried out in a batchwise or continuous mode, a continuous mode of operation is preferred. Feedstream containing CO is contacted with a reaction mixture of cuprous fluorinated acetylacetonate in organic solvent containing stabilizing agent in a stirred reaction vessel. Upon completion of removal of CO from the feed-stream, the temperature is raised, the pressure reduced or inert gas stripping agent is added to decompose the first Cu(I) complex wherein CO is replaced by $L^1$. The resulting CO is separated, the reaction vessel cooled, if necessary and fresh feedstream introduced into the reaction vessel. At temperatures below the decomposition temperature, the CO-containing cuprous complex is more stable resulting in the displacement of $L^1$. This cycle may be repeatedly carried out without Cu metal deposition.

The feedstreams may contain other inert gases such as $N_2$, $H_2$, $CO_2$, alkanes, and water vapor. $H_2S$, $SO_2$, $SO_3$ and $O_2$ should not, however, be present in amounts greater than about 10 vol%.

The invention is further illustrated by the following examples.

EXAMPLE 1

A solution of Cu(CO)(hfacac) was prepared from 10 mmoles $Cu_2O$, 20 mmoles hexafluoroacetylacetone (hfacac) and 75 ml tetrahydrofuran (THF) by bubbling CO through the solution for 20 minutes at which time the reaction was complete. Twenty mmoles of cyclooctene was added to the mixture and the solution was then heated to $40°$ C. for one hour. Infrared analysis showed that the CO was completely removed by this treatment. A CO mixture was then passed through the solution at $25°$ C. for 20 minutes and the infrared spectra indicated that the CO complex had been restored to its original concentration. Heating to $40°$ C. again caused the CO to be displaced. This sequence was repeated several times without any noticable formation of copper metal or other solids.

EXAMPLE 2

A solution of Cu(CO)(hfacac) in diethylmaleate was prepared in the same manner as described in Example 1 except that diethyl maleate was used as the solvent instead of THF. The solution, with heating to 50° C. for 30 minutes, lost almost all of its bound CO. On cooling to room temperature and passing a gas mixture containing CO through the solution for 20 minutes, the CO complex was restored to its original concentration. The process was repeated several times without any deposition of copper metal or other solids.

EXAMPLE 3

A solution of Cu(CO)(hfacac) in diethyl maleate was prepared as described in example 2. The solution containing the CO complex was then subjected to a vacuum (absolute pressure was approximately 0.05 atm) for 1 hr. during which time the solution lost almost all of its bound CO. A gas mixture containing CO was then passed through the solution for 20 minutes and the CO complex was restored to its original concentration. This process was continued through several cycles without any noticeable deposition of metallic copper.

EXAMPLE 4

A solution of Cu(CO)(hfacac) was prepared as described in example 2 except that benzonitrile was used as the solvent. Nitrogen gas was then bubbled through this solution at a rapid rate for 2 hrs. which almost entirely removed the bound CO from solution. A gas stream containing CO was subsequently passed through the depleted solution for 30 minutes restoring the CO complex to its original concentration. This process was repeated several times. COMPARATIVE EXAMPLE A solution of Cu(CO)(hfacac) was prepared from 10 mmoles Cu$_2$O, 20 mmoles hexafluoroacetylacetone and 75 ml tetrahydrofuran by bubbling a gas mixture containing 50% CO and 50% hydrogen through the solution for 1 hour at which time the reaction was complete. The solution was then heated to 60° until most of the bound CO was removed. A large quantity of copper metal was deposited and upon analysis of the green solution, it was found that the copper in solution was in the form of copper (II) hexafluoroacetylacetonate. This illustrates that in the absence of a stabilizing agent, copper deposition occurs upon CO recovery.

What is claimed is:

1. A process for separating carbon monoxide from a feedstream without copper metal formation which comprises the steps of:
    (a) contacting the feedstream with a solution of a cuprous fluorinated acetylacetonate of the formula

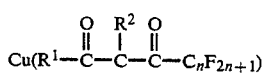

where $R^1$ is $C_1$-$C_6$ fluoroalkyl, $C_1$-$C_8$ alkyl, $C_4$-$C_6$ heterocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an organic solvent containing a stabilizing agent at a temperature sufficient to remove carbon monoxide by forming a first Cu(I) complex of the formula

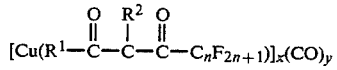

where $R^1$, $R^2$ and n are defined above, and x and y are 1 or 2, said stabilizing agent being characterized by being able to replace CO in the first Cu(I) complex thereby forming a second Cu(I) complex which is stable at temperatures wherein the first Cu(I) complex decomposes through loss of CO,
    (b) heating to a temperature sufficient to decompose the first Cu(I) complex through loss of CO whereby the stabilizing agent replaces CO in the first Cu(I) complex and copper metal formation is prevented by formation of the second Cu(I) complex, and
    (c) separating the CO.

2. The process of claim 1 wherein after separating CO and cooling, fresh feedstream is added thereby displacing the stabilizing agent from the second Cu(I) complex by reforming the first Cu(I) complex.

3. A process for separating CO from feedstreams without copper metal formation comprises the steps of:
    (a) contacting the feedstream with a solution of a cuprous fluorinated acetylacetonate of the formula

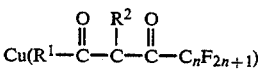

where $R^1$ is $C_1$-$C_6$ fluoroalkyl, $C_1$-$C_8$ alkyl, $C_4$-$C_6$ heterocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an organic solvent containing a stabilizing agent at a temperature sufficient to remove carbon monoxide by forming a first Cu(I) complex of the formula

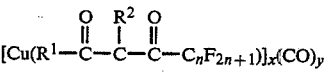

where $R^1$, $R^2$ and n are defined above, and x and y are 1 or 2, said stabilizing agent being characterized by being able to replace CO in the first Cu(I) complex thereby forming a second Cu(I) complex which is stable at pressures wherein the first Cu(I) complex decomposes through loss of CO,
    (b) reducing pressure by an amount sufficient to decompose the first Cu(I) complex through loss of CO whereby the stabilizing agent replaces CO in the first Cu(I) complex and copper metal formation is prevented by formation of the second Cu(I) complex, and
    (c) separating the CO.

4. A process for separating CO from feedstreams without copper metal formation comprises the steps of:
    (a) contacting the feedstream with a solution of a cuprous fluorinated acetylacetonate of the formula

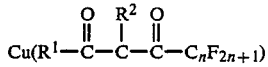

where $R^1$ is $C_1$-$C_6$ fluoroalkyl, $C_1$-$C_8$ alkyl, $C_4$-$C_6$ heterocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an organic solvent containing a stabilizing agent at a temperature sufficient to remove carbon monoxide by forming a first Cu(I) complex of the formula

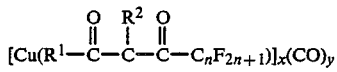

where $R^1$, $R^2$ and n are defined above, and x and y are 1 or 2, said stabilizing agent being characterized by being able to replace CO in the first Cu(I) complex thereby forming a second Cu(I) complex which is stable at pressures wherein the first Cu(I) complex decomposes through loss of CO,
  (b) reducing CO partial pressure by adding an inert gas stripping agent in an amount sufficient to strip CO from the first Cu(I) complex whereby the stabilizing agent replaces CO in the first Cu(I) complex and copper metal formation is prevented by formation of the second Cu(I) complex, and
  (c) separating the CO.

5. The process of claims 1, 3 or 4 wherein the stabilizing agent is an alkene, alkyne, isontrile, nitrile or sulfide.

6. The process of claims 1, 3 or 4 wherein the stabilizing agent is an alkene of the formula

where each $R^3$ to $R^6$ is independently H provided that at least one of $R^3$-$R^6$ is not H; $C_1$-$C_{30}$ aliphatic with the proviso that any combination of $R^3$, $R^4$, $R^5$ and $R^6$ may be joined together to form at least one $C_4$-$C_{14}$ cycloaliphatic ring; —C N; $C_6$-$C_{10}$ aryl; $C_7$-$C_{14}$ araliphatic;

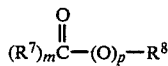

where m and p are 0 or 1, $R^7$ is $C_1$-$C_{20}$ aliphatic, and $R^8$ is H, $C_1$-$C_{10}$ aliphatic or $C_6$-$C_{10}$ aryl with the proviso that adjacent

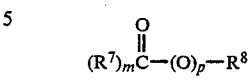

may be joined together to form a $C_4$-$C_{16}$ anhydride.

7. The process of claims 1, 3 or 4 wherein the stabilizing agent is an alkyne of the formula

where $R^9$ and $R^{10}$ are independently H; $C_1$-$C_{30}$ aliphatic; $C_6$-$C_{10}$ aryl or $C_7$-$C_{14}$ araliphatic.

8. The process of claims 1, 3 or 4 wherein the stabilizing is an isonitrile of the formula

where $R^{11}$ is $C_1$-$C_{20}$ aliphatic; $C_3$-$C_{10}$ cycloaliphatic; $C_7$-$C_{20}$ araliphatic or $C_6$-$C_{10}$ aryl.

9. The process of claims 1, 3 or 4 wherein the stabilizing agent is a nitrile or sulfide of the formulas

where $R^{12}$ to $R^{14}$ are independently $C_1$-$C_{20}$ aliphatic; $C_3$-$C_{10}$ cycloaliphatic, $C_7$-$C_{20}$ araliphatic or $C_6$-$C_{10}$ aryl.

10. The process of claims 1, 3 or 4 wherein $R^1$ is $CF_3$, $C_1$-$C_8$ alkyl which may be substituted with phenyl, $C_6$-$C_{10}$ aryl or $C_4$-$C_5$ heterocycle containing S, $R^2$ is H with the proviso that $R^1$ and $R^2$ may join together to form $C_6$ ring, and N is 1.

11. The process of claims 1, 3 or 4 wherein the fluorinated acetylacetonate is hexafluoroacetylacetone.

12. The process of claims 1, 3 or 4 wherein the stabilizing agent is also the organic solvent.

13. The process of claims 3 or 4 wherein after separating CO, fresh feedstream is added whereby the stabilizing agent is displaced from the second Cu(I) complex and CO is removed from the feedstream by reforming the first Cu(I) complex.

14. The process of claims 1, 3 or 4 wherein the cuprous fluorinated acetylacetonate solution is prepared by contacting $Cu_2O$ and fluorinated acetylacetone in an organic solvent.

* * * * *